(12) United States Patent
Hyodo et al.

(10) Patent No.: US 7,769,550 B2
(45) Date of Patent: Aug. 3, 2010

(54) STRESS ANALYSIS METHOD AND STRESS ANALYSIS APPARATUS

(75) Inventors: Koji Hyodo, Ibaraki (JP); Chao-Nan Xu, Saga (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 335 days.

(21) Appl. No.: 11/883,919

(22) PCT Filed: Jan. 11, 2006

(86) PCT No.: PCT/JP2006/000176

§ 371 (c)(1),
(2), (4) Date: Aug. 8, 2007

(87) PCT Pub. No.: WO2006/085424

PCT Pub. Date: Aug. 17, 2006

(65) Prior Publication Data

US 2008/0120045 A1 May 22, 2008

(30) Foreign Application Priority Data

Feb. 9, 2005 (JP) .............................. 2005-033124

(51) Int. Cl.
*G01L 1/00* (2006.01)
*G01L 5/00* (2006.01)
(52) U.S. Cl. ........................................................ 702/42
(58) Field of Classification Search .................. 702/34, 702/35, 40–43, 130, 136; 73/813–815, 826; 600/587; 374/100; 356/32, 33, 364, 369
See application file for complete search history.

(56) References Cited

U.S. PATENT DOCUMENTS

| 4,798,477 | A * | 1/1989 | Mountain .................... 374/45 |
| 5,817,945 | A * | 10/1998 | Morris et al. ................ 73/800 |
| 6,943,869 | B2 * | 9/2005 | Hubner et al. ................ 356/34 |
| 2001/0012920 | A1 * | 8/2001 | Ren et al. .................... 600/587 |
| 2001/0017059 | A1 * | 8/2001 | Xu et al. ...................... 73/800 |
| 2007/0186674 | A1 * | 8/2007 | Hyodo et al. ................ 73/826 |
| 2009/0012431 | A1 * | 1/2009 | Hyodo et al. ................ 600/587 |

FOREIGN PATENT DOCUMENTS

| JP | 11-120801 | 4/1999 |
| JP | 2001-215157 | 8/2001 |
| JP | 2003-137622 | 5/2003 |
| JP | 2003-139627 | 5/2003 |

* cited by examiner

*Primary Examiner*—Michael P Nghiem
(74) *Attorney, Agent, or Firm*—Rader, Fishman & Grauer PLLC

(57) ABSTRACT

A stress analysis method uses a thermoelastic stress measurement device to measure measuring stress state acting on an object by measuring material temperature state variation caused by stress, a mechanoluminescence measurement device to measure measuring stress state acting on the object by measuring light emitted from mechanoluminescence material according to the stress and an arithmetic processing device to obtain mechanical information, which includes prescribed stress distribution, by performing arithmetic processing on both the measurement data.

8 Claims, 2 Drawing Sheets

(a)

(b)

STRESS ANALYSIS METHOD AND STRESS ANALYSIS APPARATUS

CROSS-REFERENCE TO RELOCATED APPLICATIONS

This is a National Stage Application of International Application No. PCT/JP2006/300176, filed on Jan. 11, 2006, which claims the priority of Japanese Patent Application JP2005-033124, filed Feb. 9, 2005, the entire contents of which are incorporated herein by reference.

TECHNICAL FIELD

The present invention relates to a stress analysis method and stress analysis apparatus allowing the stress and strain state of an object to be perceived more in detail.

BACKGROUND ART

In order to implement a secure and safe society, it is a fundamental and indispensable element that various types of products, such as aircraft, truck, pipes of electric power plant, bridge, and an implant used in orthopedics and dentistry, have mechanical safety. Thus, stress and strain measurement technology plays an important role in implementing and evaluating product mechanical safety.

In stress distribution measurement, there has hitherto been used a strain gauge technique by which many strain gauges are attached to the surface of an object to be measured and stress/strain distribution is perceived from output signals of each strain gauge when a load is applied to the object. Using this technique, quantitative measurement can be performed, but the number of gauges attached is limited in a wide ranging measurement area or in a narrow measurement area; thus measurement having no missing point cannot be performed.

Accordingly, there has been developed and put into practical use a thermoelastic stress measurement technique (also called an infrared stress measurement technique) by which a minor temperature variation caused by thermoelastic effect when a load is applied to an object is measured by use of infrared thermography to visualize surface stress distribution. This technique is characterized by allowing two-dimensional measurement of surface stress distribution (the change in the sum of principal stresses) in a manner having no missing point, independently of whether it is a wide ranging area or a narrow area.

Meanwhile, the present applicant and others have succeeded in manufacturing, based on the research on inorganic materials emitting light according to mechanical energy, a material composed of a base material being a piezoelectric material of particularly a wurtzite structure and an inorganic material of luminescence center, as shown in Patent Document 1 described below. The patent application has been filed as a result of finding out that when this is added to the above base material, the light emitting intensity of the resultant thin film can be dramatically improved. Thereafter, as a result of further research, various inorganic materials emitting light according to such force have been found out, and at the same time the research on the use of this material in various fields has also progressed. For example, as disclosed in Patent Document 2 described below, it has been proposed that a mechanoluminescence material is preliminarily mixed into concrete in order to detect an abnormal stress produced before the concrete is broken.

Patent Document 1: JP Patent Publication (Kokai) No. 11-120801 (1999) (JP Patent No. 3265356)

Patent Document 2: JP Patent Publication (Kokai) No. 2003-137622

As described above, the thermoelastic stress measurement technique is characterized by allowing a surface stress distribution of an object to be two-dimensionally measured in a manner having no missing point. This is because, as indicated by formula (1), if a small temperature change $\Delta T$ occurring when a load is adiabatically applied to an isotropic elastic object is measured by thermography, the change in the sum of the principal stresses $\Delta\sigma$ having a proportional relation with the temperature change $\Delta T$ can be measured as an image. However, from its principle, there is an essential limitation that only the change in the sum of the surface principal stresses ($\Delta(\sigma_1+\sigma_2)$) can be measured as physical quantity, and furthermore respective principal stress components are unknown, and pure shearing stress acting on the object cannot be measured because it causes no temperature change.

$$\Delta T = -k \cdot T \cdot \Delta\sigma \quad (1)$$

$\Delta T$: the change in temperature (K)
k: the thermoelastic constant (1/Pa)
T: the object temperature (K)
$\Delta\sigma$: the change in the sum of the principal stresses (Pa)
Here, thermoelastic constant k is given by formula (2).

$$k = a/(\rho \times Cp) \quad (2)$$

a: the coefficient of linear thermal expansion (1/K)
$\rho$: density (kg/m$^3$)
Cp: the specific heat at constant pressure (J/(kg/K))

Thus, an object of the present invention is to provide a stress analysis method and stress analysis apparatus by which not only thermoelastic stress measurement but also stress measurement using a mechanoluminescence material are used in combination, whereby stress measurement can be performed more in detail while exceeding the principle limitation of thermoelastic stress measurement technique.

DISCLOSURE OF THE INVENTION

To solve the above problem, the present inventor found out the use of a material emitting light according to mechanical energy in stress measurement, the material having been previously developed as described above by the present inventor; this finding has led to the present invention. More specifically, it is a technique that uses in combination, thermoelastic stress measurement and a technique (defined as a mechanoluminescence measurement technique) by which a mechanoluminescence material is added to an object by coating, mixing or the like, and stress distribution and the like are measured by capturing light emitted according to applied load by use of a light receiving device such as a camera. More specifically, the stress analysis method according to the present invention is characterized in that: stress state acting on an object to be measured is measured by measuring material temperature state variation caused by stress; stress state acting on the object to be measured is measured by measuring light emitted from mechanoluminescence material according to the stress; and arithmetic processing is performed on both the measurement data to thereby obtain mechanical information such as prescribed stress distribution.

Another stress analysis method according to the present invention is characterized in that, in the stress analysis method, the prescribed mechanical information is normal stress component distribution information.

Another stress analysis method according to the present invention is characterized in that, in the stress analysis method, the prescribed mechanical information is shearing stress distribution information.

Another stress analysis method according to the present invention is characterized in that, in the stress analysis method, pure shearing stress distribution is outputted by use of the arithmetic processing.

The stress analysis apparatus according to the present invention is characterized by including: thermoelastic stress measurement means for measuring stress distribution acting on an object to be measured by measuring material temperature state variation caused by the stress; mechanoluminescence measurement means for measuring stress distribution acting on the object to be measured by measuring light emitted from mechanoluminescence material in response to the stress; and arithmetic processing means for obtaining mechanical information such as prescribed stress distribution by performing arithmetic processing on the data obtained by the two stress measurement means.

Another stress analysis apparatus according to the present invention is characterized in that, in the stress analysis apparatus, the prescribed mechanical information is normal stress component distribution information.

Another stress analysis apparatus according to the present invention is characterized in that, in the stress analysis apparatus, the prescribed mechanical information is shearing stress distribution information.

Another stress analysis apparatus according to the present invention is characterized in that, in the stress analysis apparatus, the arithmetic processing means outputs pure shearing stress distribution.

In measuring stress distribution of an object, stress state can be measured more in detail while exceeding the principle limitation of thermoelastic stress measurement that, for example, principal stress component values are unknown, and pure shearing stress and the like cannot be captured.

Figure 1:
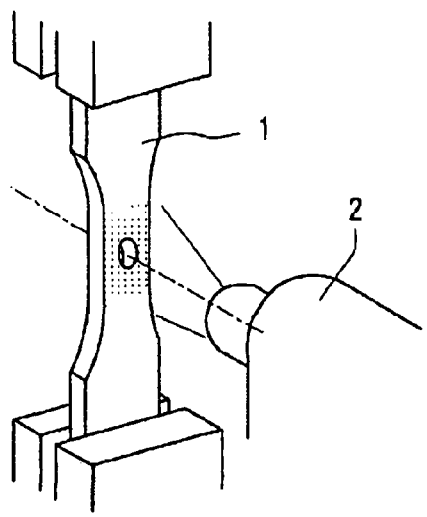
FIG. 1 is an explanatory view of an embodiment of the present invention, FIG. 1($a$) illustrating a state in which stress distribution is measured when a specimen with a circular hole is placed in a material testing machine, and FIG. 1($b$) being a functional block diagram of the present invention.
Figure 1:
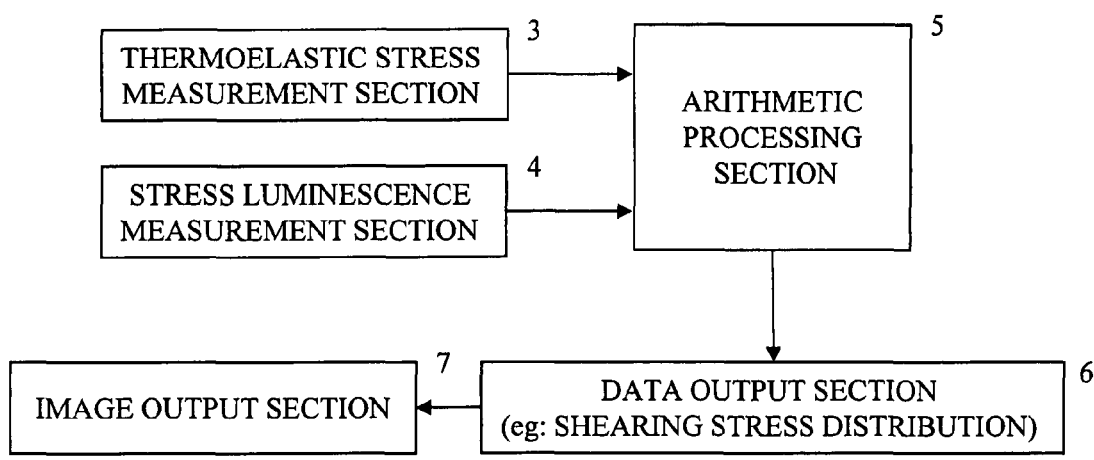

DESCRIPTION OF SYMBOLS 1 specimen
2 camera
3 thermoelastic stress measurement section
4 mechanoluminescence measurement section
5 arithmetic processing section
6 data output section
7 image output section

BEST MODE FOR CARRYING OUT THE INVENTION

The present invention is implemented by using in combination, thermoelastic stress measurement and mechanoluminescence measurement in order to measure stress distribution of an object. From the data respectively obtained and the arithmetic processing etc. using the two kinds of data, stress information that is not obtainable when either of the measurement techniques is used alone can be obtained.

EXAMPLES

By way of example, there will be described stress distribution measurement when tensile stress is applied to a plate-shaped specimen 1 with a circular hole illustrated in FIG. 1($a$). According to the present invention, a picture of, for example, the specimen 1 having tensile stress applied thereto, illustrated in FIG. 1($a$) is taken with a camera 2. In this case, a picture of temperature variation caused by stress and strain acting on the specimen 1 is taken with the conventionally used thermoelastic stress measurement camera 2, and furthermore a picture of a mechanoluminescence material added to the specimen 1, emitting light according to stress is taken. As the cameras used herein, separate ones can be used; but the pictures may be taken with a single camera.

From the image data thus captured, thermoelastic stress distribution is measured by a thermoelastic stress measurement section 3 illustrated in FIG. 1($b$), and mechanoluminescence distribution is measured by a mechanoluminescence measurement section 4. An arithmetic processing section 5 performs arithmetic processing, such as subtraction processing, on the measurement data. The arithmetic result is outputted, for example as an image from a data output section 6 to an image output section 7, and displayed as an image on a monitor or the like.

Figure 2:
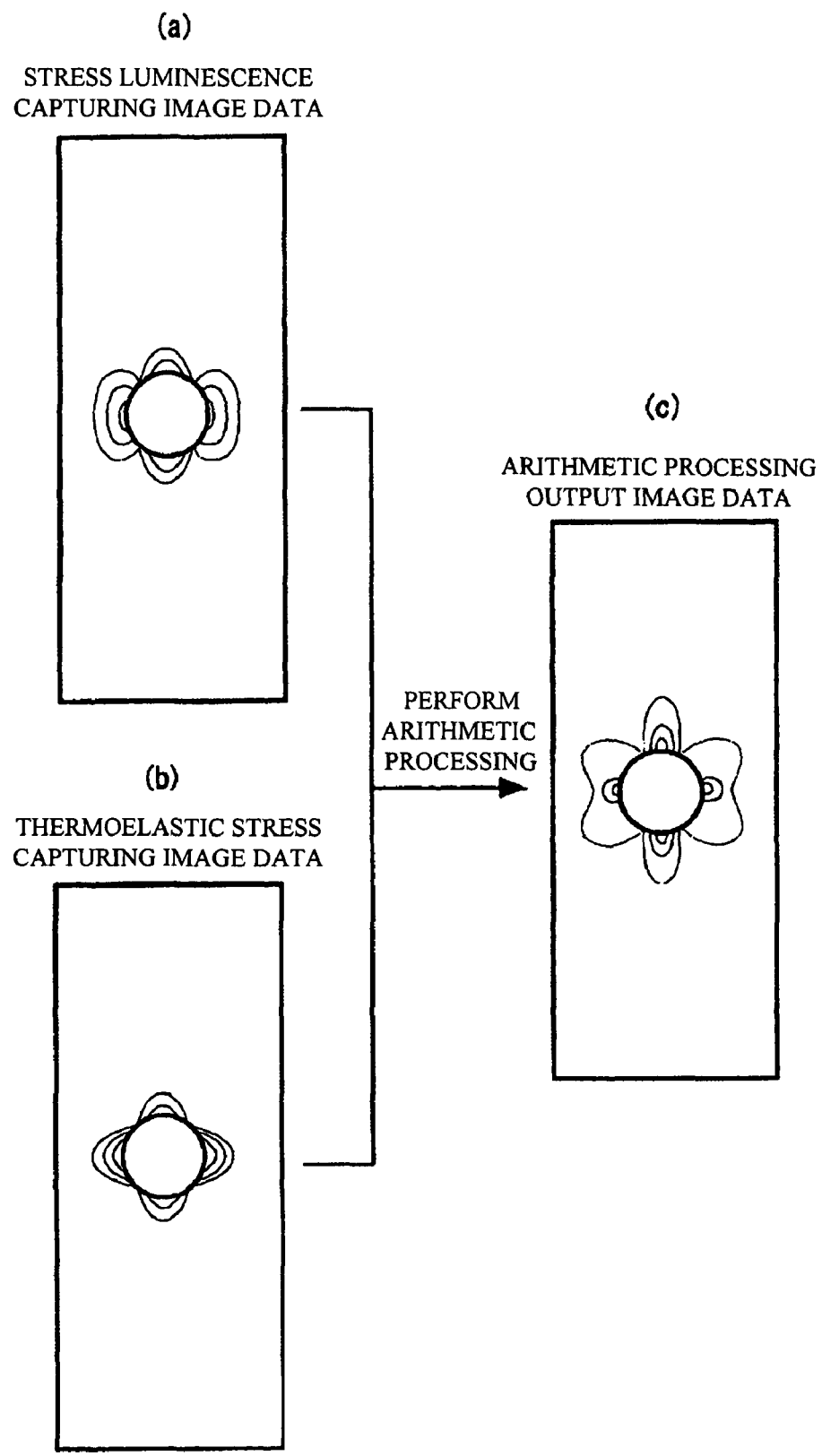
FIG. 2 is an explanatory view illustrating a state according to the present invention in which mechanoluminescence capturing image data and thermoelastic stress capturing image data are subjected to arithmetic processing to obtain prescribed mechanical information.

FIG. 2 schematically illustrates an example in which tensile stress is applied to the above plate-shaped specimen 1 with a circular hole. From mechanoluminescence capturing image data illustrated in FIG. 1($a$), thermoelastic stress capturing image data ($\Delta(\sigma_1+\sigma_2)$ image) is calculated, whereby stress information illustrated in FIG. 1($c$), which cannot be obtained when either of the measurement techniques is used alone, can be known; for example, principal stress component values ($\sigma_1$ and $\sigma_2$) can be known, or shearing stress etc. can be obtained. An exemplary fundamental theory of the present invention will be described below.

(1) Physical quantity which cannot be measured from the principle limitation when either of the measurement techniques is used alone, for example, principal stress component values ($\sigma_1$ and $\sigma_2$) can be obtained by combining the two techniques.

The surface stress of a sample (isotropic elastic body) will be studied as a plane stress condition. Strain values $\epsilon_1$ and $\epsilon_2$ dependent on principal stress values $\sigma_1$ and $\sigma_2$ can be expressed as follows.

$$\epsilon_1 = 1/E \times (\sigma_1 - \nu\sigma_2) \tag{1}$$

$$\epsilon_2 = 1/E \times (\sigma_2 - \nu\sigma_1) \tag{2}$$

where E is the modulus of longitudinal elasticity, and $\nu$ is Poisson's ratio.

Also, elastic energy u is expressed as follows.

$$u = 1/2 \times (\sigma_1\epsilon_1 + \sigma_2\epsilon_2) \tag{3}$$

Thus, when formulas (1) and (2) are applied to formula (3), $$u = 1/2E \times (\sigma_1^2 + \sigma_2^2) - \nu/E \times \sigma_1\sigma_2 \tag{4}$$

$$= 1/2E \times (\sigma_1^2 + \sigma_2^2 - 2\nu\sigma_1\sigma_2) \tag{5}$$

$$= 1/2E \times ((\sigma_1 + \sigma_2)^2 - 2\sigma_1\sigma_2 - 2\nu\sigma_1\sigma_2) \tag{6}$$

Also, since the change in the sum of the principal stresses can be measured by the thermoelastic stress measurement technique, when the obtained value is defined as A, $$\sigma_1+\sigma_2=A \quad (7)$$

$$\sigma_2=A-\sigma_1 \quad (8)$$

When these are applied to formula (6), $$u=((1+\nu)/E)\times\sigma_1^2-(A(1+\nu)/E)\times\sigma_1+(A^2/2E) \quad (9)$$

When this formula is transformed, $$((1+\nu)/E)\times\sigma_1^2-(A(1+\nu)/E)\times\sigma_1+((A^2/2E)-u)=0 \quad (10)$$

Thus, the quadratic equation of $\sigma_1$ is obtained.

Since elastic energy u is information obtained by the mechanoluminescence technique, the three coefficients of this equation are known values.

$$(1+\nu)/E=B \quad (11)$$

$$-A(1+\nu)/E=C \quad (12)$$

$$(A^2/2E)-u=D \quad (13)$$

Therefore, when formula (10) being the quadratic equation of $\sigma_1$ is solved, σ1 and σ2 can be determined as follows.

$$\sigma_1=(-C\pm(C^2-4BD)^{1/2})/(2B) \quad (14)$$

$$\sigma_2=A-\sigma_1 \quad (15)$$

The plus-minus sign in formula (14) can be uniquely determined from the absolute value or calibration. It is noted that this result may also be expressed as follows.

$$(\sigma_1,\sigma_2)=(-C\pm(C^2-4BD)^{1/2})/(2B) \quad (16)$$

The above process can be calculated based on the two-dimensional image obtained by the thermoelastic stress measurement technique and mechanoluminescence technique, and its result can be displayed as an image. Also, using formulas (1) and (2), strain values can be displayed; or principal shearing stress can be calculated and displayed. Furthermore, if principal axis direction is obtained from the distribution of the principal stress component etc., development into the analysis by Mohr's stress circle is also possible.

There will now be considered an example in which only pure shear is applied to an object. In this case, when τ is shearing stress and γ is shearing strain, elastic energy u is $$u=\tfrac{1}{2}\times(\tau\gamma) \quad (17)$$

Here, when G is shear modulus of elasticity, the following formula is obtained.

$$\gamma=1/G\times\tau \quad (18)$$

When this is applied to formula (17), the following formula is obtained.

$$u=\tfrac{1}{2}G\times\tau^2 \quad (19)$$

Consequently, from formula (19), the following formula is obtained.

$$\tau=\pm(u\times 2G)^{1/2} \quad (20)$$

In a pure shear condition, there is no physical quantity that can be measured by the thermoelastic stress measurement technique; but the value of elastic energy u can be known by the mechanoluminescence measurement. Accordingly, the value of shearing stress τ can be two-dimensionally perceived from formula (19). The plus-minus sign can also be uniquely determined by calibration.

The present invention can be applied to various fields in which stress distribution is preferably measured. For example, when a mechanoluminescence material is added by mixing, coating or the like to a product or model produced by a three-dimensional modeling apparatus or the like, and the thermoelastic stress measurement and mechanoluminescence measurement are performed, then the present invention can be applied to detailed surface stress analysis, checking of stress concentration area, and the like in order to prevent breakage, fatigue failure or the like.

Also, when a mechanoluminescence material is added by coating or the like to a component produced by cutting machining or the like, and the thermoelastic stress measurement and mechanoluminescence measurement are performed, detailed surface stress analysis can be performed. The present invention can be applied to checking of stress concentration area in order to prevent breakage, fatigue failure or the like.

Also, in a simulation such as finite element method, the accuracy is determined by the closeness of the boundary condition setting to the real one. The stress component of the real one is checked by performing the thermoelastic stress measurement and mechanoluminescence measurement to optimize the boundary condition etc. of the simulation, whereby the accuracy can be improved.

For example, when the measurement is performed for a simulated bone having attached thereto an implant for orthopedics or dentistry, its detailed surface stress distribution can be known; this can be applied to more detailed mechanical compatibility evaluation of the implant.

Further, when the thermoelastic stress measurement and mechanoluminescence measurement are performed by use of, for example, a magnifying optical system such as an (infrared) microscope, the present invention can be applied to high-accuracy stress analysis of a microscopic area that cannot be measured by conventional techniques such as a micro machine.

Also, when an optically transparent material is used in both the techniques, not only surface stress but also internal stress can be measured.

INDUSTRIAL APPLICABILITY

The present invention can be applied to a wide range of industrial fields in which stress measurement is needed, because stress distribution can be measured in detail while exceeding the principle limitation of thermoelastic stress measurement technique.

The invention claimed is:

1. A stress analysis method using a stress analysis apparatus including thermoelastic stress measurement mechanism, mechanoluminescence measurement mechanism, and arithmetic processing mechanism, the method comprising the steps of:
   using the thermoelastic stress measurement mechanism to measure stress state acting on an object by measuring material temperature state variation caused by stress;
   using the mechanoluminescence measurement mechanism to measure stress state acting on the object by measuring light emitted from mechanoluminescence material added to the object according to the stress; and
   using the arithmetic processing mechanism to obtain mechanical information by performing arithmetic processing on both the measurement data, wherein the mechanical information includes prescribed stress distribution.

2. The stress analysis method according to claim 1, wherein the prescribed mechanical information is normal stress component distribution information.

3. The stress analysis method according to claim 1, wherein the prescribed mechanical information is shearing stress distribution information.

4. The stress analysis method according to claim 1, wherein pure shearing stress distribution is outputted by use of the arithmetic processing.

5. A stress analysis apparatus comprising:
- thermoelastic stress measurement means for measuring stress state acting on an object by measuring material temperature state variation caused by stress;
- mechanoluminescence measurement means for measuring stress state acting on the object by measuring light emitted from mechanoluminescence material added to the object according to the stress; and
- arithmetic processing means for obtaining mechanical by performing arithmetic processing on the data obtained by the two stress measurement means, wherein the mechanical information includes prescribed stress distribution.

6. The stress analysis apparatus according to claim 5, wherein the prescribed mechanical information is normal stress component distribution information.

7. The stress analysis apparatus according to claim 5, wherein the prescribed mechanical information is shearing stress distribution information.

8. The stress analysis apparatus according to claim 5, wherein the arithmetic processing means outputs pure shearing stress distribution.

* * * * *